United States Patent [19]
Koike et al.

[11] Patent Number: 5,507,811
[45] Date of Patent: Apr. 16, 1996

[54] PROSTHETIC DEVICE FOR ATRIAL SEPTAL DEFECT REPAIR

[75] Inventors: Kazuyuki Koike, Tokyo; Yoshkazu Kishigami, Ootsu, both of Japan

[73] Assignee: Nissho Corporation, Osaka, Japan

[21] Appl. No.: 339,557

[22] Filed: Nov. 15, 1994

[30] Foreign Application Priority Data

Nov. 26, 1993 [JP] Japan .................................. 5-321353

[51] Int. Cl.⁶ .................................................. A61F 2/00
[52] U.S. Cl. ......................... 623/11; 606/151; 606/157; 606/215
[58] Field of Search ............... 623/11, 13; 606/151, 606/157, 213, 215, 220

[56] References Cited

U.S. PATENT DOCUMENTS

| | | | |
|---|---|---|---|
| 3,874,388 | 4/1975 | King et al. | 128/334 R |
| 4,710,192 | 12/1987 | Liotta et al. | 623/11 |
| 4,917,089 | 4/1990 | Sideris | 606/215 |
| 5,108,420 | 4/1992 | Marks | 606/213 |
| 5,290,217 | 3/1994 | Campos | 606/151 |
| 5,334,217 | 8/1994 | Das | 606/213 |
| 5,368,602 | 11/1994 | de la Torre | 606/151 |
| 5,379,754 | 1/1995 | Tovey et al. | 606/151 |

FOREIGN PATENT DOCUMENTS

0541063A2  5/1993  European Pat. Off. .

OTHER PUBLICATIONS

Gladwin s. Das et al., *Circulation*, vol. 88, No. 4, Part 1, Oct. 1993, "Experimental atrial Septal Defect Closure With a New, Tanscatheter, Self-Centering Device."

Primary Examiner—David H. Willse
Assistant Examiner—Bruce E. Snow
Attorney, Agent, or Firm—Ronald J. Kubovcik

[57] ABSTRACT

A prosthetic device to occlude an opening present in a defective atrial septum, the device having at least two clips for firmly gripping peripheral portions around the opening. The material further has a flat occluder to close the opening, and at least two fastening means for securing the clips to the flat occluder. The prosthetic device can be applied to the defective atrial septum permanently and easily in an percutaneous-transvascular manner.

3 Claims, 5 Drawing Sheets

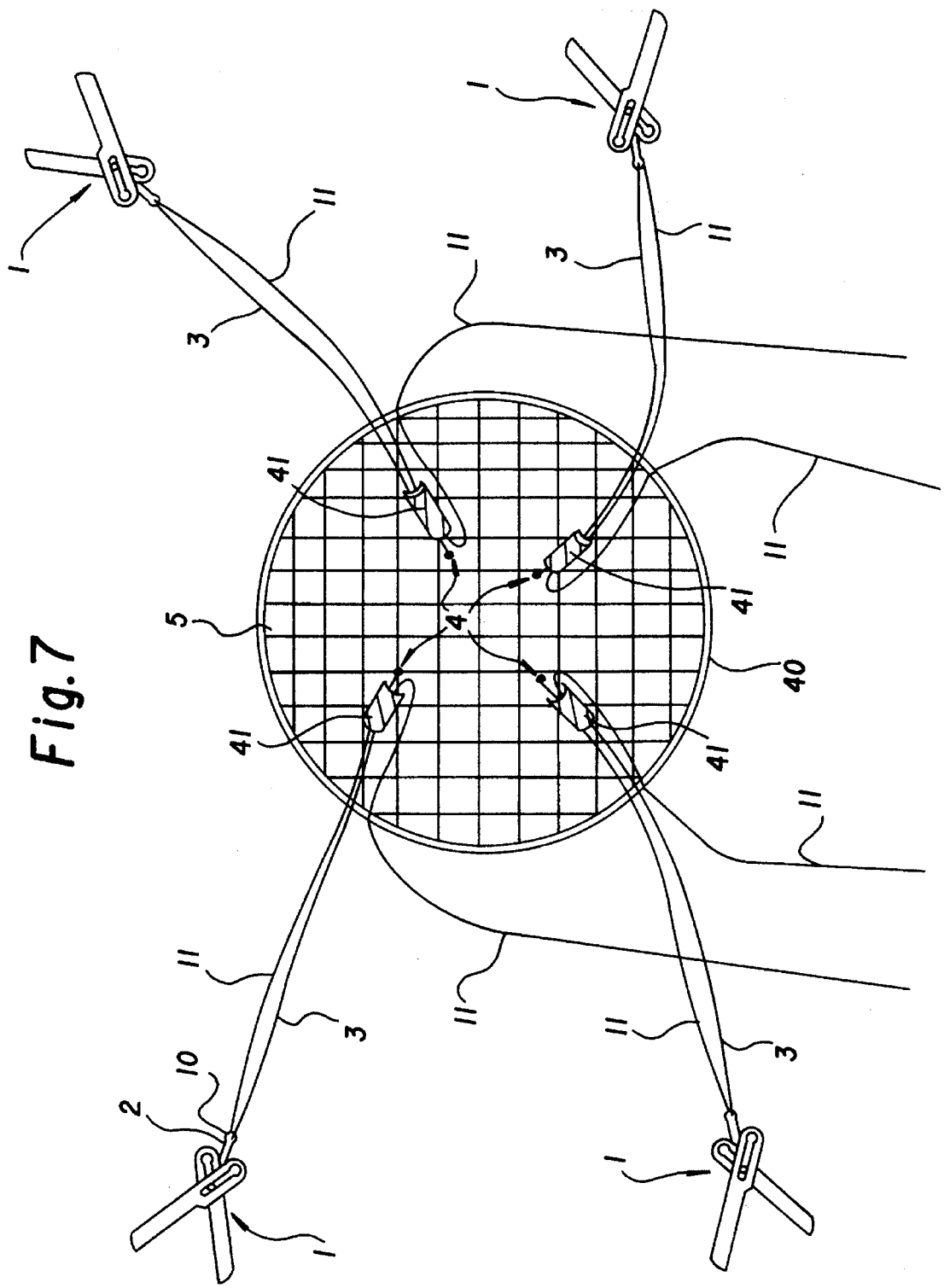

PROSTHETIC DEVICE FOR ATRIAL SEPTAL DEFECT REPAIR

BACKGROUND OF THE INVENTION

1. Field of the Invention

The present invention relates to a prosthetic device used in the repair of atrial septal defects. More particularly, it relates to a prosthetic device which will be brought in an percutaneous and transvascular manner through a catheter and up to a defective opening of a septum present between the right and left atria.

2. Prior Art

In 1976, King and Mills reported their treatment of an atrial septal defect [JAMA, 235, 2506 (1976)]. In this first successful case wherein a prosthetic device was brought through a catheter up to the septum in an percutaneous-transvascular manner, they used a pair of umbrella-shaped disk members which were disposed in the right atrium and left atrium, respectively. A tool employed in their operation was an assembly of a central wire and two catheters coaxially combined with one another. The disk members sandwiching the septum were fixed one to the other to close the defective opening thereof. It is noted, however, that their catheters were so large in diameter and the disk members were so stiff that this operation could not be performed on young children, particularly not preschool children. Rashkind, who had tried to provide a smaller-sized device, reported in 1977 his successful clinical procedure performed on a young child patient [Circulation, 67,711 (1983)]. He used a clogging material of the single-umbrella type having hooks. The hooks, however, were highly likely to cause a jamming of the umbrella-like material, wherein the clogging material once opened within a heart could never be displaced therein or removed therefrom. In such an event, doctors would have to perform open heart surgery. He then proposed an improved device comprising two umbrella-shaped members united integrally with each other, and this device has been widely used in the clinical treatment of the patent ductus arteriosus.

On the other hand, Lock, who had improved Rashkind's device of the double and integral disk type, added a coiled spring to an intermediate portion of each of eight stainless steel ribs. The two disks capable of tightly overlapping one another can now firmly grip a thin septum present between the atria. He has filed a patent application for his improved system (see EP 0 541 063 A2). Lock's device having the umbrella-like disks resembling as a whole a clam, viz. one species of Bivalvia, is called a "clamshell umbrella". A long sheath of the 11F type catheter is inserted into a patient's femoral vein, so that Lock's device can be used for any patient who weighs 8 Kg or more. Thus, Lock's method is virtually the first clinical success in the surgical remedy of atrial septal defect wherein percutaneous-transvascular catheters are used.

Some parts such as hinges and arms of the stainless steel ribs in Lock's umbrella were, however, found broke soon after arrangement in the patient's heart, due to metal fatigue or deterioration in strength occurring in vivo. Therefore, the clinical testing was interrupted recently in the U.S.A. and in Japan. Further, it is almost impossible for Lock's umbrella to be placed in the center of the opening in the defective septum. In order to compensate for an offset of the umbrella from the center of the opening, the former must be twice as large as the latter, increasing the length of stainless steel ribs required.

SUMMARY OF THE INVENTION

An object of the present invention, which has been made to eliminate the described drawbacks, is to provide a novel prosthetic device that can be placed on a defective atrial septum in an percutaneous-transvascular manner to thereby permanently occlude an opening in the septum.

In order to achieve the object, the prosthetic device provided herein includes at least two clips for firmly gripping peripheral portions around an opening present in a defective atrial septum; a flat occluder to close the opening present in the septum; and at least two fastening means for securing the clips to the flat occluder.

The flat occluder may be a piece of fabric selected from a group consisting of a woven fabric, a knitted fabric and a nonwoven fabric, all the fabrics being biocompatible (non-reactive, non-thrombotic and preferably, suitable substrates for endtheliagation).

The occluder may have a rim integral with and extending around the occluder.

Each fastening means can include a string having a distal end which is secured to the occluder at a peripheral portion thereof facing the clip, and forms a return path to the peripheral portion of the occluder so as to penetrate an aperture formed therein backwards through a catheter which delivers the clip into the heart and exteriorizes at the proximal end thereof. Pulling the string back can combine the clip and the occluder tightly.

Alternatively, each fastening means can include a pair of pieces fitting one in another or screw-threaded pieces mating one another.

BRIEF DESCRIPTION OF THE DRAWINGS

In the drawings showing an embodiment of the present invention,

FIG. 7 is an explanatory drawing of prosthetic device in another example.

DETAILED DESCRIPTION OF THE INVENTION

Figure 1:
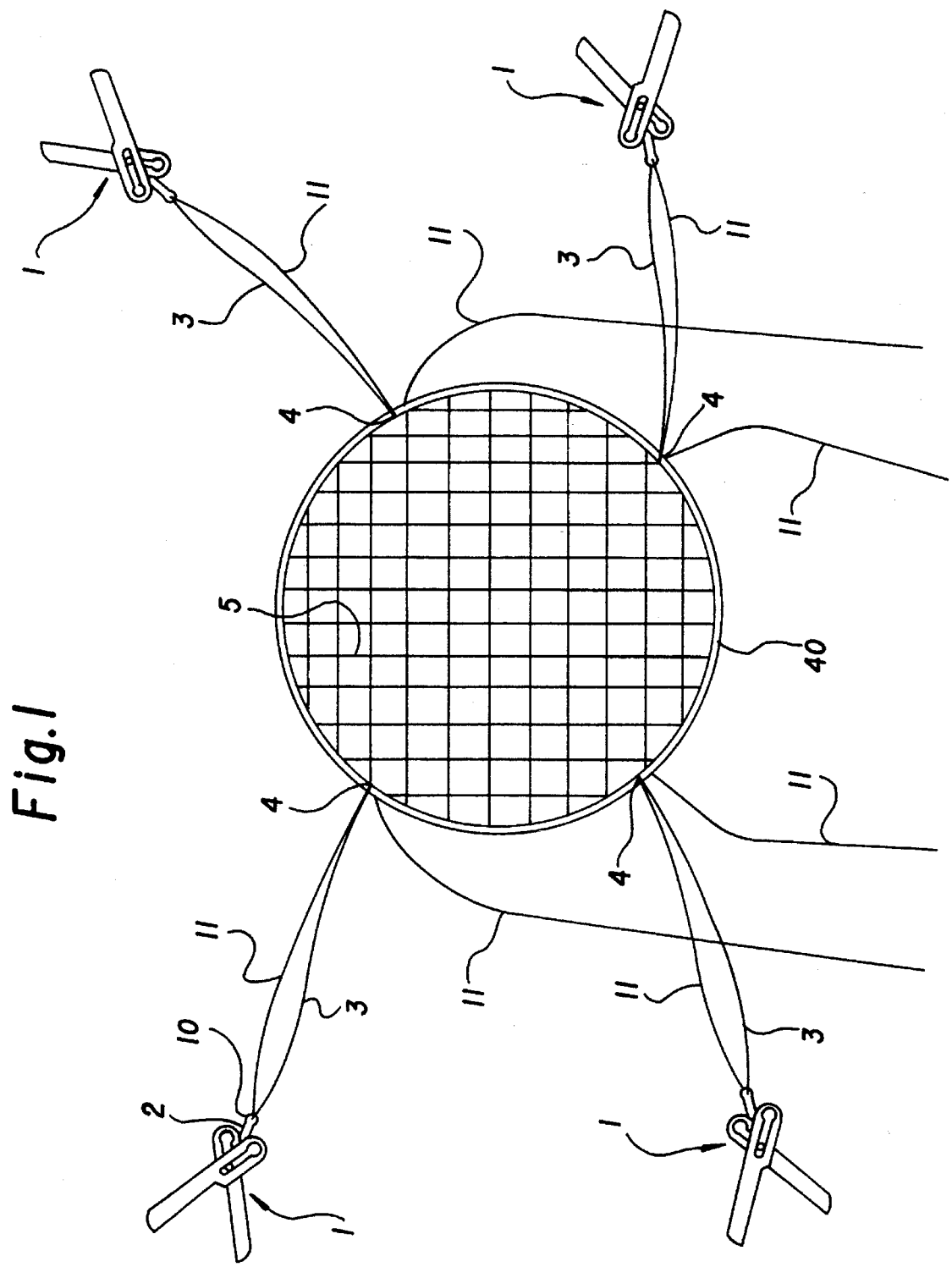
FIG. 1 is a plan view of a prosthetic device provided in the embodiment and comprising clips.

An embodiment of the present invention will now be described referring to the drawings, wherein a prosthetic device is provided. This device shown in the drawings comprises: clips 1; knobs 2; strings 3; apertures 4 in occluder 5; a delivery catheter 6 for delivering the clips; a long sheath 7; heads 8 of the knobs; round recesses 9; and a rim 40.

Figure 2:
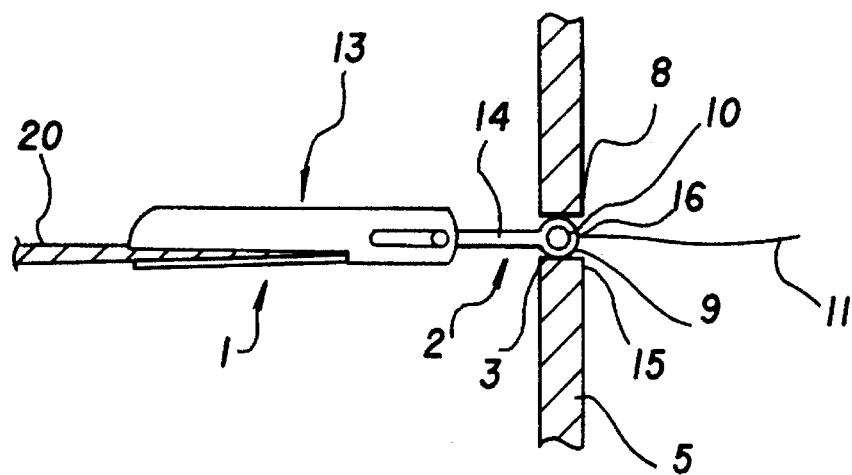
FIG. 2 is a cross-sectional view showing one of the clips which has gripped a peripheral portion around an opening present in a defective atrial septum.
Figure 6:
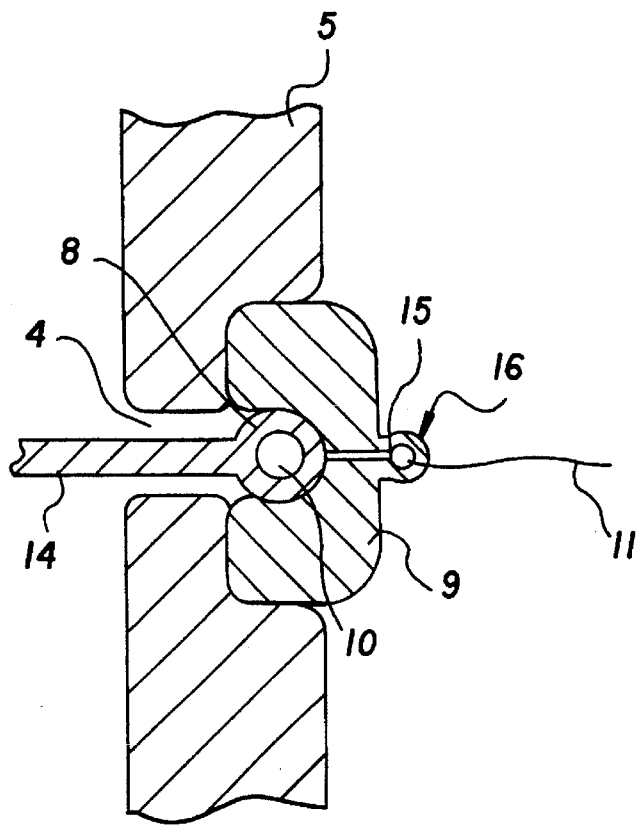
FIG. 6 is an enlarged drawing near the round recess in FIG. 2.

In the embodiment shown in FIG. 1 and FIG. 6, the prosthetic device comprises the occluder 5 which is generally round and has a ring-shaped reinforcing rim 40. Each of the four strings 3 penetrates the corresponding one of four apertures 4. The strings 3 are held by small bores 10, which are formed through the heads 8 of knobs 2 extending from the clips 1. A distal end of each string is a loose knot thereof or is engaged with a discrete retainer located at a side of the occluder 5, at the reverse side of clip 1 to the occluder 5. Another end or proximal portion of each string 3 forms a return portion 11 to extend through the aperture 4 or a portion adjacent thereto of the occluder 5. The proximal portions further advance through the long sheath 7 and beyond its proximal extremity. Thus, the four return portions 11 may be pulled one by one so that the occluder 5 moves towards the clips 1, until firmly adjoined thereto to close an opening present in a defective atrial septum. Each retainer in FIG. 1 (not shown) may the round recess 9 formed in the peripheral edge of the occluder 5 as seen in FIG. 2. The recesses fit on the heads 8 of knobs 2 extending from the clip 1. The peripheral edge of the occluder will be anchored in this manner by the knob heads to the clips gripping the defective septum. The occluder 5 thus secured to the septum will close the opening thereof.

The ring-shaped rim 40 shown in FIG. 1 is attached to the peripheral portion of the flat occluder 5 so that it can readily be fixed on the portion around the opening present in the defective septum. Alternatively, the rim may be formed using a suturing thread to hem a piece of a woven, knitted or nonwoven fabric. The size of the occluder 5 must be at least 105%, or more preferably 110–150% by area of the opening in the defective septum.

FIG. 2 illustrates one of the clips shown in FIG. 1, when it has just gripped the peripheral portion around the opening present in the defective atrial septum 20. FIG. 6 is an enlarged drawing near the round recess 9 in FIG. 2. Each clip 1 comprises a gripping portion 13 and the knob 2, which in turn comprises a sliding rod 14 and the head 8. Each string 3 penetrating the small bore 10 in the head 8 is held thereby and is displaceable relative thereto. The string 3 has a distal end which has passed through the aperture 4 of the occluder 5, and then through a bottom of the round recess 9 so as to terminate as a knot 16 fixed to the occluder 5. On the other hand, the return portion 11 of the string is held movable through the small bore 10 in the head 8, penetrates the aperture 4 or an adjacent portion of the occluder 5, and then penetrates the bore 15 in the bottom of recess 9. A proximal end of the return portion extends backward through the long sheath 7 and protrudes from its end opening. The head 8 of the knob 2 will thus be fitted in the round recess 9 so that the occluder 5 is tightly combined with the clips 1 gripping the periphery which surrounds the opening in the defective atrial septum 20.

The flat occluder 5 as the principal part may be a piece of fabric, a film, a porous sheet, or a composite material thereof, so long as they are biocompatible. The material may be made of synthetic polymers including a polyester such as polyethylene terephthalate; a polyolefin such as polyethylene and polypropylene; a polyamide such as Nylon 6 and Nylon 66; a fluoride resin such as polyethylene fluoride and polyvinylidene fluoride; a chloride resin such as polyvinylidene chloride; and a polyurethane. Alternatively, the material may be made of a semi-synthetic resin such as a cellulose derivative; or a natural fiber. The rim 40 secured to the periphery of the occluder 5 may be made of a metal, a ceramic or a synthetic resin. Preferably, the rim is made of a super-elastic alloy such as Ni—Ti alloy and Cu—Al—Ni alloy.

The string 3 including its return portion 11 may be a natural or synthetic suturing thread or a biocompatible monofilament.

Figure 3:
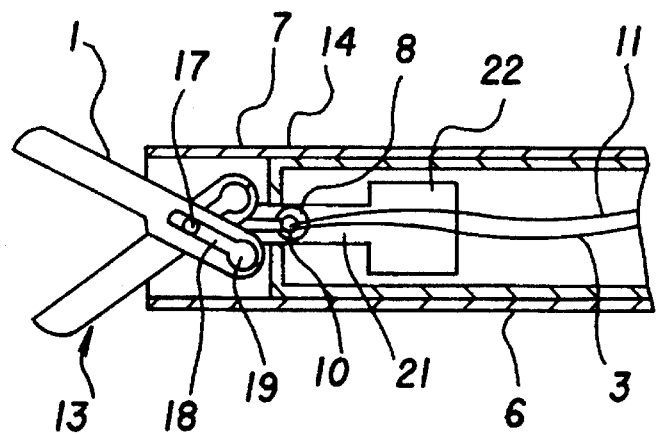
FIG. 3 is a cross section of an operative catheter carrying the clip.

FIG. 3 shows the delivery catheter 6 which carries at its distal end the clip 1. The gripping portion 13 of the clip consists of a pair of scissors-shaped pieces each having at its basal end a small slot 18, and a pivot 17 in a sliding engagement with the slots. A basal end of each small slot 18 is formed as a retaining recess 19 to lock the pivot. The pivot 17 irreversibly fits in the retaining recesses 19 when the scissors-shaped pieces grip the peripheral portion around the opening present in the septum. Once the scissors-shaped pieces grip the peripheral portion, the pivot 17 can no longer slide within the slots 18 so as to open the pieces. This pivot is integral with the knob 2 and is a distal end of the sliding rod 14 thereof which has at its proximal end the head 8. Thus, to close the scissors-shaped pieces the string engaging with the small bore 10 in the head 8 is pulled. This pulling displaces the sliding rod 14 of the knob 2 and causes the pivot 17 to slide backward in the slot 18.

The gripping portion 13 of the clip is positioned outside the distal end of the delivery catheter 6 which operates the clip. The knob head 8 of the clip is positioned inside said distal end. The sliding rod 14 connecting the gripping portion 13 to the head 8 slides in a guide slot 21 formed in the distal end and longitudinally of the catheter 6. An escape zone 22 is formed integral with and at the rear end of the guide slot 21 which is of a length corresponding to the sliding rod 14. Thus, the knob 2 will disengage from the delivery catheter 6 when twisted or otherwise locked within the long sheath 7 after the knob head 8 is retracted into the escape zone 22.

In use of the prosthetic device to close an opening present in a defective septum, a catheter introducer of a desired diameter will be inserted percutaneously to the peripheral vein. A thinner tube and then thicker tubes will be used for this purpose in a manner as shown, for example, in Japanese Unexamined Patent Publication No. 3-195533. An outer catheter of the largest diameter will be placed through the fistula. A long sheath 7 is subsequently inserted into the catheter introducer until it reaches a patient's heart via the femoral vein. A contrast medium may be supplied through the long sheath so as to obtain a visual X-ray image to determine the position, size and number of the openings in the defective atrial septum. Additionally or alternatively, an echographic transmitter may be set in the patient's esophagus or in the long sheath, to take an ultrasound tomographic image to determine the position of said openings.

Subsequent to this determination, an end of the long sheath 7 is directed to the defective atrial septum. Then, a delivery catheter 6 is inserted in the inner catheter as shown in FIG. 3. Each clip 1 carried by a distal end of the delivery catheter 6 is manually operable therethrough. In detail, the clips 1, the number of which is for example four as shown in FIG. 1, is operated each by the string 3 and the return portion 11 thereof. Thus, the respective peripheral portions around the opening in the septum are firmly gripped by the clips. The delivery catheter 6 is then removed out of the long sheath 7, so that the distal ends of strings 3 respectively engaging with the clips 1 are inserted through the apertures 4 of the occluder. Subsequently, the occluder 5 is placed into the long sheath 7, and the return portion 11 of each string is pulled backward so as to locate the occluder 5 closest to the clips 1. The distal ends of the strings 3 inserted through the apertures 4 of the occluder 5 have loose knots. These knots are then unfastenably tied to the return portion 11, thereby permanently securing the occluder 5 to the clips 1. After the occluder 5 has closed in this way the opening in the defective septum, an excessive proximal end of each return portion 11 of the string is severed and removed from the remainder thereof.

In operation, the distal end of delivery catheter 6 travels into a distal region of the long sheath, with the gripping portion 13 of clip being closed but not locked closed. The gripping portion thus takes its position adjacent to the opening of the defective septum, and an operator subsequently pulls the return portion 11 of the string. As a result, gripping portion 13 seizes the periphery around the opening, and simultaneously the pivot 17 snaps in the aligned retaining recesses 19 at the ends of small slots 18. At this stage, the knob head 8 of the clip 1 is in the escape zone 22 and is released from the delivery catheter 6, which in turn is subsequently withdrawn from the long sheath 7. It will be understood that at this stage the proximal end of each string 3 protruding outwardly of the fistula is still outside the patient's body. The string end penetrates the aperture 4 in the peripheral edge of the occluder 5, such that it extends through the bore 15 formed in the bottom of round recess 9 which is located opposite to the clip. The knot of the string protruding outwardly from the bore 15 immovably engages with the outer surface of the recess bottom which the bore penetrates. On the other hand, the return portion 11 of this string lying through the small bore 10 in the knob head 8 is also guided through the aperture 4 so as to penetrate the other bore 15 in the bottom of round recess 9. The proximal end of the return portion 11 is located outside the inlet of the fistula and therefore can be pulled by the operator.

The above description has been made taking as an example one string penetrating one aperture 4 in the flat occluder. However, the generally round occluder 5 as shown in FIG. 1 has four apertures 4 arranged along its periphery. Correspondingly, four strings 3 and four return portions 11 thereof respectively penetrate those apertures. The four return portions 11 are pulled together to insert the occluder 5 accompanied by the strings 3 into the long sheath 7, until the apertures 4 reach the knob heads 8 of the clips 1. By further pulling the return portions 11, the knob heads 8 are fitted in the round recesses 9 in the occluder 5 arranged opposite to the clips 1, in a manner shown in FIG. 2 such as to urge the occluder towards the clips until it closes the opening in the defective atrial septum. As a final step of this operation, a cutter with a scissors-shaped end will be put into the long sheath 7 in order to sever the excessive length of string from each return portion 11. FIG. 7 is an explanatory drawing of prosthetic device in another example. The prosthetic device comprises the occluder 5 on which each connector 41 is installed near each of four apertures 4. Each of the four strings 3 penetrate the corresponding one of four apertures. The strings 3 are held by small bores 10, which are formed through the heads of knobs 2 extending from the clips 1. A distal end of each string is a loose knot thereof or is engaged with a discrete retainer located at a side of the occluder 5, with the side not facing the clip 1. Another end or proximal portion of each string 3 forms a return portion 11 to extend through the aperture 4 or a portion adjacent thereto of the occluder. A distal end of each string 3 is secured by a knot thereof to the occluder 5 adjacent to the center side of the connector 41. The string penetrates the aperture of the corresponding connector 41 another end or proximal portion is held by a small bore 10, which is formed through the head of the knob 2 extending from the clip, forms a return portion 11 to extend through the aperture 4 in the connector 41.

Figure 8:
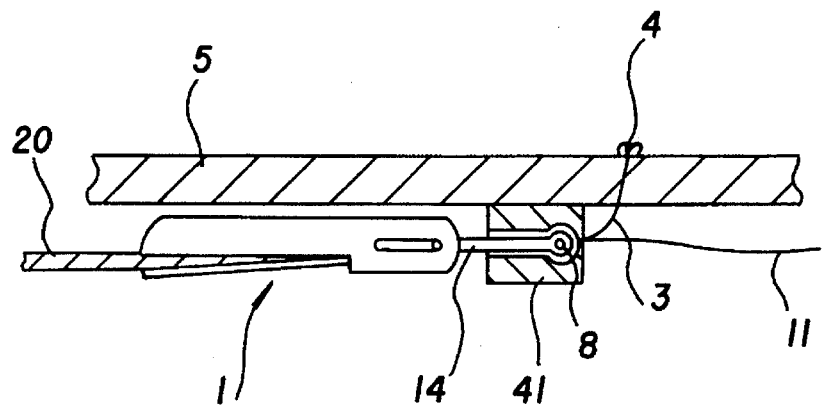
FIG. 8 is an explanatory drawing showing one of the clips which has gripped a peripheral portion in FIG. 7.

FIG. 8 illustrates one of the clips shown in FIG. 7 when it has just gripped the peripheral portion around the opening present in the defective atrial septum 20. Each connector 41 in FIG. 7 has a round recess 9 at the central side therein as seen in FIG. 8. Each string 3 penetrating the small bore 10 in the head 8 is held thereby and is displaceable relative thereto. The string 3 has a distal end which has passed through the aperture 4 of the occluder 5, and then through a bottom of the round recess 9 so as to terminate as a knot fixed to the occluder 5. On the other hand, the return portion 11 of the string which is held movable through the small bore 10 in the head 8, penetrates the aperture 4 of the connector 41. A proximal end of the return path extends away from clip 1, through the long sheath 7 and protrudes from its end opening. The head 8 of the knob 2 will thus be fitted in the round recess 9 in the central side of the connector 41 so that the occluder 5 is tightly combined with the clips 1 gripping the periphery which surrounds the opening in the defective atrial septum 20.

Figure 4:
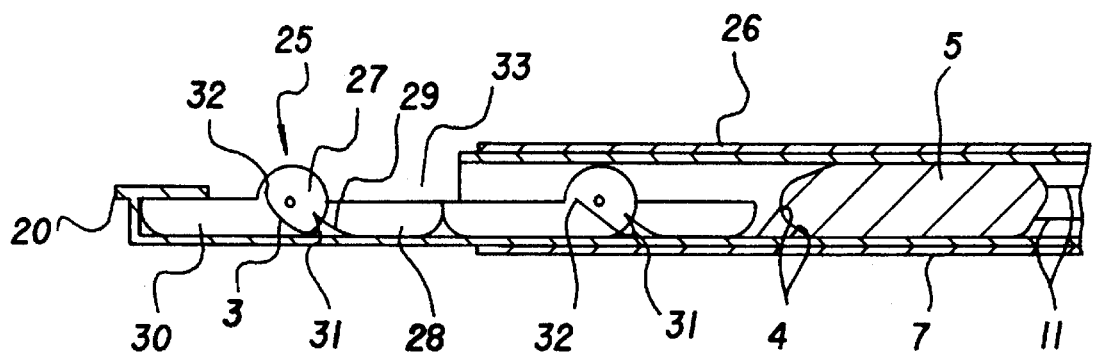
FIGS. 4 and 5 illustrate a modified example of the operative catheter carrying at its distal end, for example, two modified clips.

FIG. 4 illustrates a modified operative catheter similarly having clips. Each clip 25 is in its horizontally opened state at the distal end of the catheter 26. Hinge portions 27 of upper and lower arms of the clip 25 comprise a ratchet mechanism which allows the arms to make a one-way motion towards each other to close the clip. An end of a string 29 is fixed on the hinge portion 27 of the upper arm 28. When the string is pulled, the upper arm 28 rotates towards and overlies the lower arms 30 to provide a hook 31 for gripping the periphery of the opening in the septum. A bore 32 for holding the string 3 opens through the proximal region of the hinge portion 27. One end of the string 3 extends through one of the apertures 4 in the occluder 5 to form a knot which anchors the string to the occluder. The delivery catheter 26 for operating the clips has at its distal end a window 33 where the upper arm 28 of the clip 25 rotates.

Figure 5:
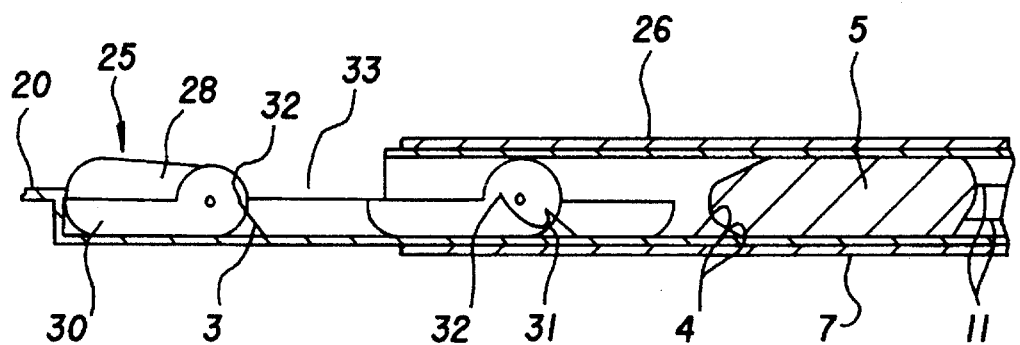

In operation, the delivery catheter 26 takes a position in the long sheath 7 such that the window 33 is located outside the distal end of long sheath 7. The lower arm 30 of clip 25 is positioned near the defective septum, before the strings 29 attached to the hook 31 are pulled. The upper arm 28 will thus rotate to overlie the lower one 30 to thereby grip the periphery around the opening present in the septum. In FIGS. 4 and 5, two clips 25 are shown in connection with the delivery catheter 26, though it normally carries four clips and one flat occluder 5. Those clips 25 are operated one by one in the manner described above to grip the periphery 20 around the opening present in the septum. Subsequently, the return portions 11 extending through small bores 32 formed in the clips 25 are pulled backward so that the flat occluder 5 moves towards the clips. Thus, the occluder 5 fastened in this manner to the clips tightly closes the opening in the septum, before finally removing the excessive lengths of each return portion 11 and each string 29.

In summary, the prosthetic device comprises the flat biocompatible occluder 5, and clips cooperating with the occluder, wherein the clips grip the septum periphery around the opening and cause the occluder to come into alignment with and close the opening. There is no problem of setting the occluder offset with respect to the center of the opening, unlike the prior art device comprising two umbrella-shaped sheets. It is also not necessary to use an occluder twice as large as the opening, and there is no fear of breakage of springed ribs due to deterioration or fatigue thereof because the present device does not contain any springed rib. The prosthetic device provided herein can be applied to the defective atrial septum permanently and easily in an percutaneous-transvascular manner.

What is claimed is:

1. A prosthetic device to occlude an opening present in a defective atrial septum, the device comprising:

at least two clips for firmly gripping peripheral portions around the opening;

a flat occluder to close the opening present in the septum; and at least two fastening means for securing the clips to the flat occluder, wherein the occluder comprises a piece of a biocompatible fabric having a reinforcing rim extending therearound, each fastening means comprising a string having a distal end which is secured to the occluder at a peripheral portion thereof, the string extending through an aperture formed in the said peripheral portion.

2. A prosthetic device according to claim 1, wherein the fabric is selected from the group consisting of a woven fabric, a knitted fabric and a nonwoven fabric.

3. A prosthetic device according to claim 1, wherein each fastening means further includes a pair of catheters fitting one in another.

* * * * *